US006349790B1

(12) United States Patent
Brimhall

(10) Patent No.: US 6,349,790 B1

(45) Date of Patent: Feb. 26, 2002

(54) SELF-CLEANING CERUMEN GUARD FOR A HEARING DEVICE

(75) Inventor: Owen D. Brimhall, South Jordan, UT (US)

(73) Assignee: Sonic Innovations, Inc., Salt Lake City, UT (US)

( * ) Notice: Subject to any disclaimer, the term of this patent is extended or adjusted under 35 U.S.C. 154(b) by 0 days.

(21) Appl. No.: 09/592,222

(22) Filed: Jun. 12, 2000

Related U.S. Application Data

(63) Continuation of application No. 09/287,228, filed on Apr. 6, 1999.

(51) Int. Cl.[7] .................................................. A61B 7/02

(52) U.S. Cl. ....................... 181/135; 181/130; 181/129; 181/134; 381/322; 381/328

(58) Field of Search ................................ 181/135, 130, 181/129, 134, 128, 126, 133; 381/322, 328, 312, 325, 330, 68, 68.6, 68.7, 69, 138

(56) References Cited

U.S. PATENT DOCUMENTS

| | | | | |
|---|---|---|---|---|
| 3,665,122 A | | 5/1972 | Weiss | 179/107 BC |
| 4,375,016 A | | 2/1983 | Harada | 179/182 R |
| 4,553,627 A | * | 11/1985 | Gastmeier et al. | 181/135 |
| 4,569,812 A | | 2/1986 | Werwath et al. | 264/222 |
| 4,756,312 A | | 7/1988 | Epley | 128/420.5 |
| 4,879,750 A | | 11/1989 | Nassler | 381/68.6 |
| 4,880,076 A | | 11/1989 | Ahlberg et al. | 181/130 |
| 4,937,876 A | * | 6/1990 | Biermans | 381/68.6 |
| 5,002,151 A | | 3/1991 | Oliveira et al. | 181/130 |
| 5,031,219 A | | 7/1991 | Ward et al. | 381/68.6 |
| 5,084,224 A | | 1/1992 | Watters | 264/155 |
| 5,099,947 A | * | 3/1992 | Guggenberger et al. | 181/130 |
| 5,105,904 A | | 4/1992 | Olsen | 181/128 |
| 5,166,659 A | | 11/1992 | Navarro | 381/68.6 |
| 5,201,007 A | | 4/1993 | Ward et al. | 381/68.6 |
| 5,203,352 A | * | 4/1993 | Gardner, Jr. | 128/864 |
| 5,293,008 A | * | 3/1994 | Danielsen | 181/135 |
| 5,327,500 A | | 7/1994 | Campbell | 381/68.6 |
| 5,395,168 A | | 3/1995 | Leenen | 381/68.6 |
| 5,401,920 A | | 3/1995 | Oliveira | 181/135 |
| 5,440,082 A | | 8/1995 | Claes | 181/135 |
| 5,682,020 A | * | 10/1997 | Oliveira | 181/130 |
| 5,701,348 A | | 12/1997 | Shennib et al. | 381/68.6 |
| 5,881,159 A | | 3/1999 | Aceti et al. | 381/328 |
| 5,920,636 A | | 7/1999 | Oliveira et al. | 381/328 |
| 5,996,584 A | | 12/1999 | Oliveira et al. | 128/864 |
| 6,000,492 A | * | 12/1999 | Puthuff et al. | 181/135 |

FOREIGN PATENT DOCUMENTS

| | | | |
|---|---|---|---|
| EP | 0 835 042 A2 | 4/1998 | H04R/25/02 |

* cited by examiner

*Primary Examiner*—Robert E. Nappi
*Assistant Examiner*—Edgardo San Martin
(74) *Attorney, Agent, or Firm*—Lyon & Lyon LLP

(57) ABSTRACT

A self-cleaning cerumen guard includes a thermally activated element. The cerumen guard is mounted on the distal end of a hearing device adjacent to a sound port. The thermally activated element is oriented in a manner which causes it to retract when heated to a first temperature range and extend when cooled to a second temperature range, such that, upon removal of the hearing device from an ear canal, the self-cleaning cerumen guard will automatically remove any accumulated debris from the sound port.

9 Claims, 7 Drawing Sheets

SELF-CLEANING CERUMEN GUARD FOR A HEARING DEVICE

RELATED APPLICATION DATA

This application is a continuation of co-pending U.S. patent application Ser. No. 09/287,228, filed on Apr. 6, 1999.

FIELD OF THE INVENTION

The present invention pertains to hearing aids. More particularly, the present invention pertains to cerumen guards for hearing aids.

BACKGROUND OF THE INVENTION

The modern trend in the design and implementation of hearing devices is focusing to a large extent on reducing the physical size of the hearing device. Miniaturization of hearing device components is becoming increasingly feasible with rapid technological advances in the fields of power supplies, sound processing electronics and micro-mechanics. The demand for smaller and less conspicuous hearing devices continues to increase as a larger portion of our population ages and faces hearing loss. Those who face hearing loss also encounter the accompanying desire to avoid the stigma and self consciousness associated with this condition. As a result, smaller hearing devices which are cosmetically less visible are increasingly sought after.

Hearing device technology has progressed rapidly in recent years. First generation hearing devices were primarily of the Behind-The-Ear (BTE) type, where an externally mounted device was connected by an acoustic tube to a molded shell placed within the ear. With the advancement of component miniaturization, modern hearing devices rarely use this Behind-The-Ear technique, focusing primarily on one of several forms of an In-The-Canal hearing device. Three main types of In-The-Canal hearing devices are. routinely offered by audiologists and physicians. In-The-Ear (ITE) devices rest primarily in the concha of the ear and have the disadvantages of being fairly conspicuous to a bystander and relatively bulky to wear. Smaller In-The-Canal (ITC) devices fit partially in the concha and partially in the ear canal and are less visible but still leave a substantial portion of the hearing device exposed. Recently, Completely-In-The-Canal (CIC) hearing devices have come into greater use. As the name implicates, these devices fit deep within the ear canal and are essentially hidden from view from the outside.

In addition to the obvious cosmetic advantages these types of in-the-canal devices provide, they also have several performance advantages that larger, externally mounted devices do not offer. Placing the hearing device deep within the ear canal and proximate to the tympanic membrane (ear drum) improves the frequency response of the device, reduces distortion due to jaw extrusion, reduces the occurrence of the occlusion effect and improves overall sound fidelity.

The anatomy of the ear canal includes ceruminous glands which secrete a yellowish, wax-like substance called cerumen (ear wax). Cerumen tends to accumulate in the ear canal. Due to both the action of cilia located within the ear canal and the natural movements of the ear canal, the cerumen gradually propagates outward. When a hearing device is inserted into the ear canal, it is susceptible to the effects of cerumen accumulation. Cerumen can often mix with sloughed off skin and dirt, further impairing operation of the hearing device.

With the onset of smaller and more sophisticated hearing devices, the buildup of cerumen can have more severe effects on their performance. Receivers (i.e., an acoustic speaker) utilized in most modern hearing devices are particularly susceptible to performance problems and damage from cerumen accumulation. Initially, cerumen accumulation physically blocks the receiver port occluding the acoustic path and preventing sound waves from efficiently reaching the tympanic membrane. Eventually, the cerumen can penetrate into the receiver housing and damage the sensitive mechanical and electrical components located within the housing. Most of these internal components are critical to the operation of the hearing device and their failure will necessitate repair or replacement of the hearing device. The monetary and time costs associated with replacing failed hearing devices due to cerumen clogging and receiver damage is significant.

U.S. Pat. No. 5,401,920, entitled “Cerumen Filter For Hearing Aids” (“the ’920 patent”), discloses a replaceable and disposable wax guard that is affixed over the sound port of an in-the-ear hearing aid by means of a pressure sensitive tape. The filter itself is porous to sounds but is receptive to cerumen. While providing some level of protection against cerumen damage to the internal components of the hearing device, this and other similar types of “filters” become quickly soiled, resulting in poor device performance due to a blocked receiver port. As such, the disposable filter must be frequently replaced by the user. The small size of these devices often requires a high level of visual acuity and dexterity for such maintenance.

U.S. Pat. No. 5,327,500, entitled “Cerumen Barrier for Custom In The Ear Type Hearing Instruments” (“the ’500 patent”), discloses a cerumen barrier for a custom, in the ear type hearing instrument. The cerumen barrier consists of a small door covering the receiver port which can be manually rotated open to provide cleaning under the door and around the receiver port. While also providing some level of protection against cerumen to the internal components of the hearing device, the ’500 patent also requires significant user intervention to clean the filter.

Various other devices, and particularly those described in U.S. Pat. No. 4,879,750, entitled “Hearing Aid With Cerumen Trapping Gap,” U.S. Pat. No. 5,105,904, entitled “Cerumen Trap For Hearing Aid,” and U.S. Pat. No. 5,166, 659, entitled “Hearing Aid With Cerumen Collection Cavity,” utilize various types of trapping mechanisms to collect cerumen. However, in each of these devices the cerumen is simply collected and a user must still manually clear it from the device.

SUMMARY OF THE INVENTION

The present invention is directed to a self-cleaning cerumen guard, which includes a thermally activated element. In a preferred embodiment, the cerumen guard is mounted on the distal end of a hearing device adjacent to a sound port. The thermally activated element is oriented in a manner which causes it to maintain a first shape in a first temperature range and a second shape in a second temperature range, such that, upon removal of the hearing device from an ear canal, the cerumen guard will automatically remove any accumulated debris from the sound port.

Other and firther aspects and advantages of the invention will become apparent hereinafter.

BRIEF DESCRIPTION OF THE DRAWINGS

The drawings illustrate both the design and utility of the preferred embodiments of the present invention, in which similar elements in different embodiments are referred to by the same reference numbers for purposes of ease in illustration of the invention, wherein.

DETAILED DESCRIPTION OF THE PREFERRED EMBODIMENTS

Figure 1:
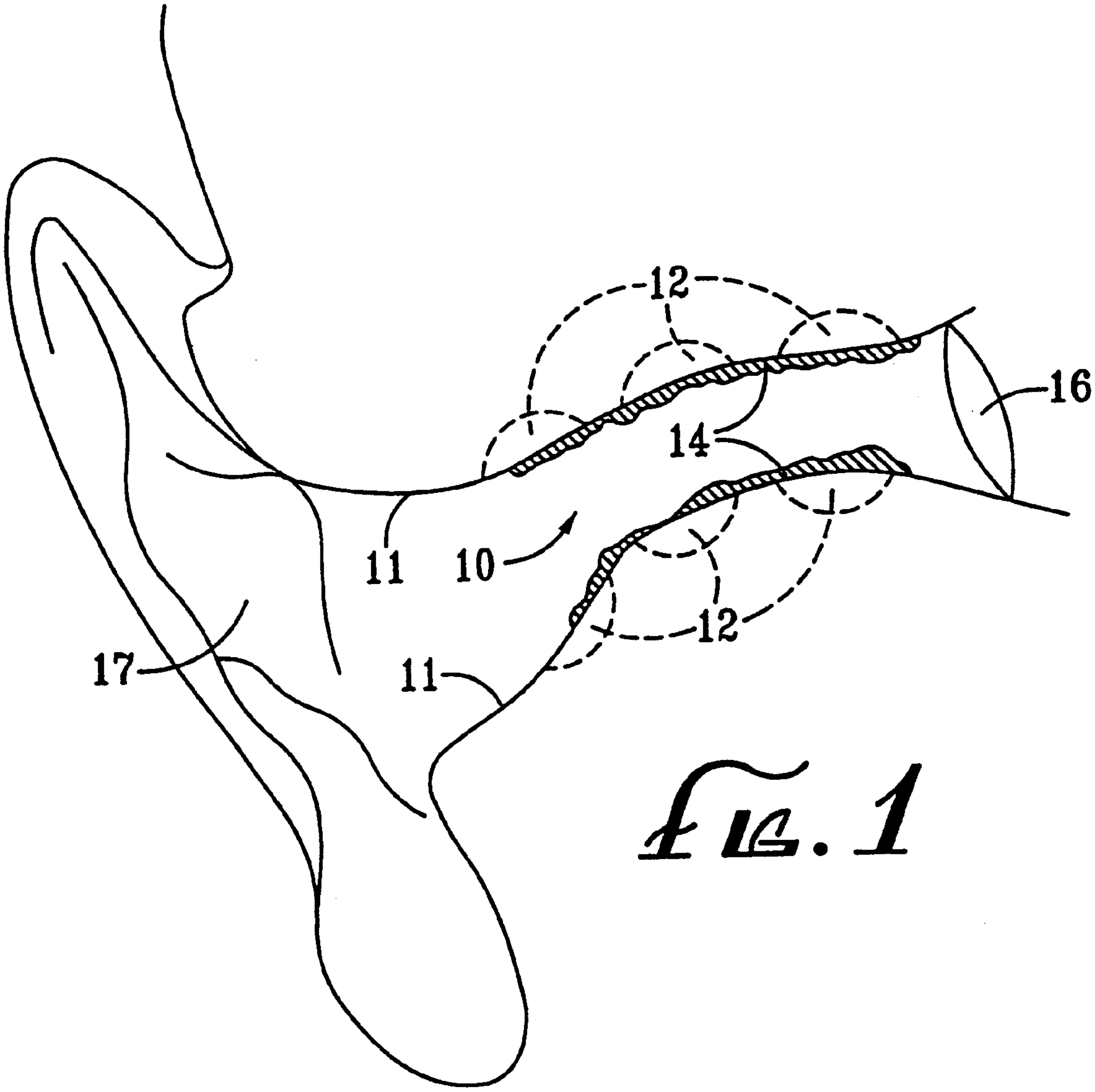
FIG. 1 is a cut away section of an ear canal and its associated anatomy.

FIG. 1 illustrates the general anatomy of an ear. Generally, the ear includes a canal 10 with fleshy walls 11, ceruminous glands 12, a tympanic membrane 16 (ear drum) and a concha 17. The ceruminous glands 12 secrete a yellowish wax-like substance called cerumen 14 (ear wax), which accumulates within the ear canal 10 and, most particularly, along the fleshly walls 11. Cerumen 14 naturally propagates outward from the inner portions of the ear canal 10 towards the concha 17. This outward movement is due in part to the action of tiny cilia (not shown) located along the ear canal walls 11 and in part to the natural movements of the ear canal 10.

The tympanic membrane 16 is located at the deepest portion of the ear canal, and transmits acoustic energy into the inner ear where it is eventually interpreted by the brain as sounds.

Figure 2:
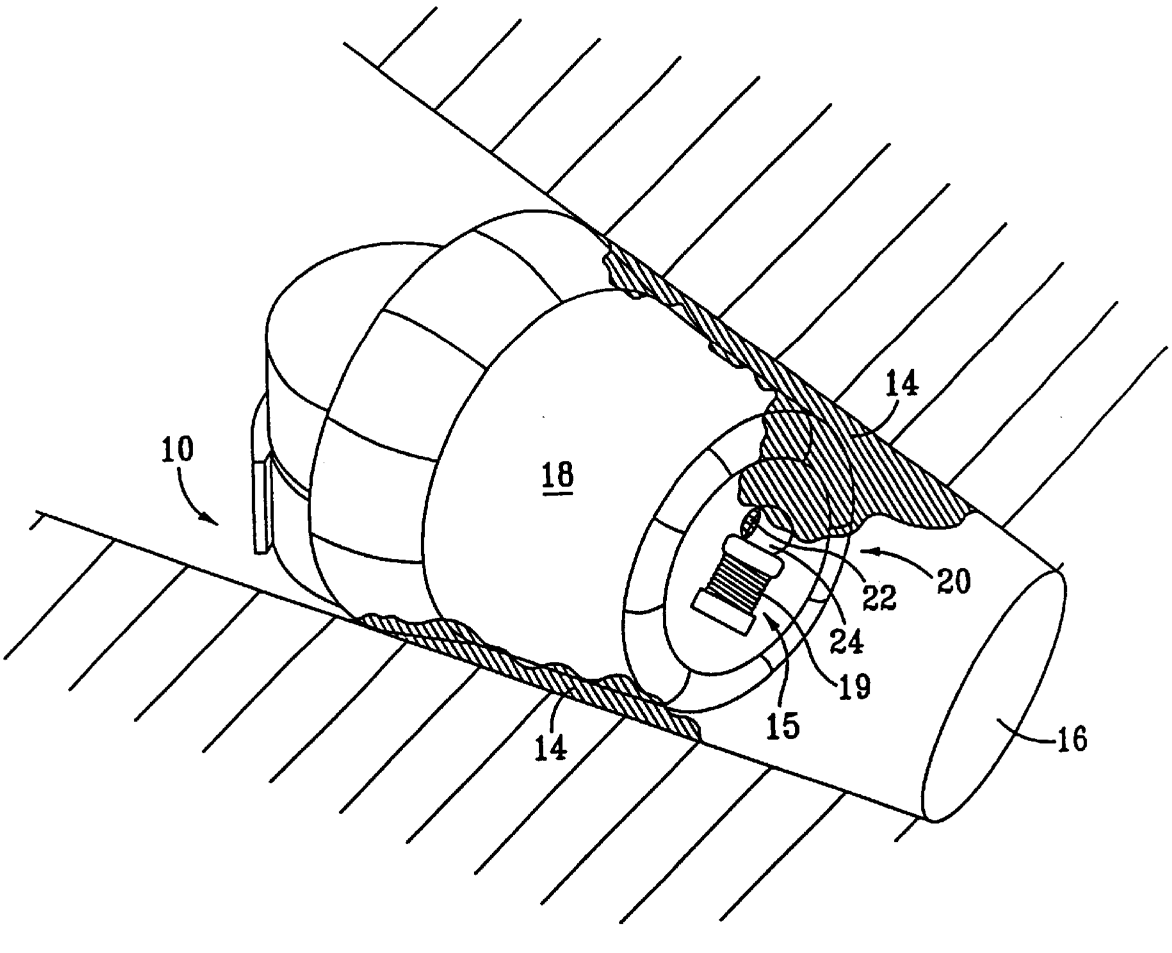
FIG. 2 is a perspective view of a first preferred embodiment of an in-the canal hearing device seated within an ear canal and utilizing a self-cleaning cerumen guard constructed in accordance with the present invention.

FIG. 2 illustrates how cerumen accumulation can interfere with the operation of an in-the-canal hearing device 18. While FIG. 2 illustrates a completely-in-the-canal (CIC) hearing device 18, this is by example only and similar problems exist with the use of most other types of hearing devices.

The in-the-canal hearing device 18 forms an acoustic seal between the tympanic membrane 16 and the external environment beyond the concha 17. Located on a distal end 20 of the hearing device 18 is a sound port 24 covered by a filter 22. Also mounted on the distal end 20 is a first preferred self-cleaning cerumen guard 15, constructed in accordance with the present invention. When cerumen 14 becomes trapped by the hearing device 18, or is secreted beyond the distal end 20, it eventually blocks the sound port 24. Maintaining a clear acoustic path is essential to the proper operation of the hearing device 18. Thus, when the sound port 24 becomes even partially obstructed, the efficiency and performance of the hearing device 18 is affected. In accordance with a main aspect of the present invention, the self-cleaning cerumen guard 15 minimizes or eliminates this problem by automatically wiping away cerumen 14 and other debris from the sound port 24.

The cerumen guard 15 includes a thermally activated element 19 which cycles between an extended position and a retracted position upon the change in temperature that occurs when the hearing device is inserted or removed from the ear canal 10. In this manner, the sound port 24 is automatically cleared of debris each time the hearing device 18 is removed from the ear canal 10. The need for user intervention is thereby greatly reduced or eliminated.

The thermally activated element 19 can comprise various geometrical configurations and can be formed from several different types of thermally activated materials. For example, the properties of basic thermal expansion and contraction present in many common metallic materials can be utilized so that the geometry of the thermally activated element will change gradually and continuously over a specified temperature range. The thermally activated element can therefore be fully extended when it reaches a first temperature and fully retracted when it reaches a second temperature. At intermediate temperatures, the thermally activated element will be at an intermediate position. Depending on the application, the geometry of the thermally activated element can be formatted to either extend or retract upon an increase in temperature.

Other types of thermally activated materials, such as bimetallics, exhibit a more discrete geometric change. These types of materials will change from one configuration to another as their temperature changes from one range to another. Similarly, the material will return to its previous configuration when its temperature returns to the first range. These temperature ranges tend to remain consistent whether the material temperature is increasing or decreasing. In certain materials, these two temperature ranges may actually abut one another so that the thermally activated element changes from one shape to another at a discrete point.

Yet another group of thermally activated materials include those that undergo a phase transition upon a change in temperature. These materials transition from one phase, such as a solid, to another phase, such as a liquid, when their temperature changes from one range to another. These temperature ranges also tend to remain consistent whether the material temperature is increasing or decreasing. These two temperature ranges may actually abut one another so that the thermally activated element changes from one shape to another at a discrete point.

The material properties of the thermally activated element 19 can therefore vary, depending on the application and corresponding choice of material. Examples of commercially available materials which may be utilized include shape memory alloys (e.g., nitinol), bimetallics, phase change polymers, phase change waxes and thermally expanding liquids in expandable bellows. Of particular importance is that the thermally activated material can be configured to extend and retract when moved between a cooler (e.g., "ambient room temperature") environment and an warmer (e.g. "body temperature") environment.

Figure 3A:
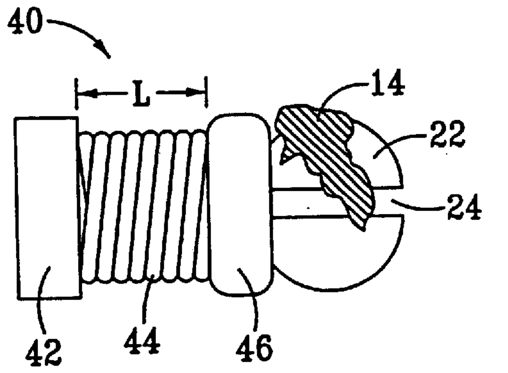
FIGS. 3A and 3B are top and side views, respectively, of a first preferred embodiment of a self-cleaning cerumen guard constructed in accordance with the present invention, shown in a retracted position.
Figure 3B:
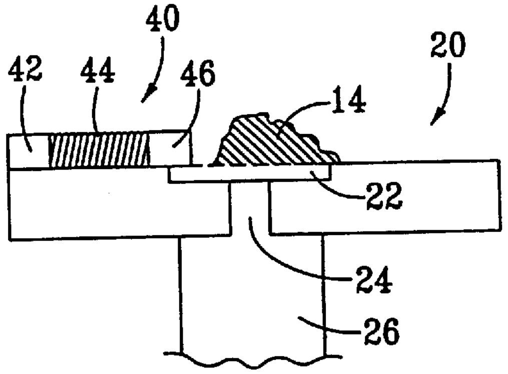

Referring to FIGS. 3A and 3B, a first preferred self-cleaning cerumen guard 40 constructed in accordance with the present invention is shown. A spring 44 connects a base 42 to a plunger 46. FIGS. 3A and 3B show the self-cleaning cerumen guard 40 in a retracted state. While seated within a users ear canal 10, the self-cleaning cerumen guard 40 remains in this retracted state and does not obstruct the acoustic path to the sound port 24. As shown in FIGS. 3A and 3B, the sound port 24 is blocked by a piece of cerumen 14, typical of the situation where a hearing device has been positioned in an ear canal for an extended period of time.

Figure 4A:
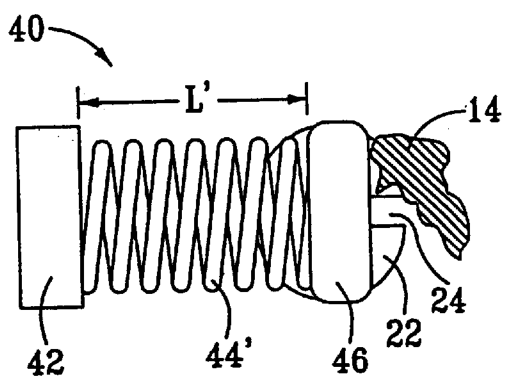
FIGS. 4A and 4B are top and side views, respectively, of the cerumen guard of FIGS. 3A and 3B, shown in an extended position.
Figure 4B:
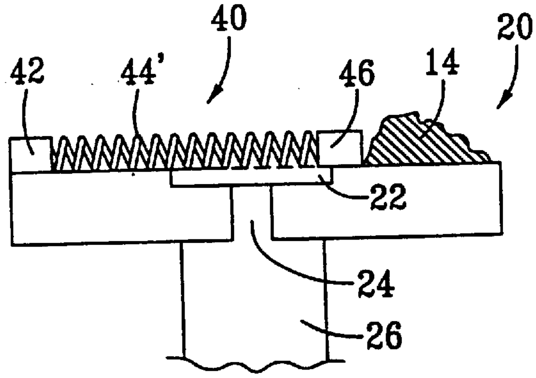

Turning now to FIGS. 4A and 4B, the cerumen guard 40 is shown in an extended state. In particular, when activated by a decrease in temperature, the spring 44 extends into what is shown in FIGS. 4A and 4B as reference number 44'. This extension forces the plunger 46 across the sound port 24, thereby removing any accumulated cerumen 14 or other debris from the acoustic path. The spring 44 is oriented so that it will extend upon a decrease in temperature. As such, when the hearing device 18 is removed from the ear canal 10 and exposed to (normally) cooler temperatures, the spring 44 extends and the plunger 46 is forced across the distal end 20 of the hearing device 18.

Conversely, when the hearing device 18 is inserted into the ear canal 10, the resulting increase in temperature causes the spring 44 to retract, thereby moving the plunger 46 away from the sound port 24. The acoustic path is therefore unobstructed when the hearing device 18 is in operation within a user's ear canal. As an example, the thermally activated material may be designed so that it will retract when its temperature reaches a first range point (e.g., 90° F. and lower or "room temperature") and extend when its temperature reaches a second range (e.g., 95° F. or higher or "body temperature"). As will be appreciated by those of ordinary skill in the art, the particular temperatures at which the spring 44 extends or retracts may be varied. For instance, if a user lives in a warmer climate, the spring 44 should be configured so that it extends at a higher temperature.

In one embodiment, where the action of the spring is based on simple thermal expansion and contraction, the spring 44 will gradually extend and retract when moved between two temperature ranges and is preferably formatted so that it will be fully extended when removed from the ear canal (i.e., room temperature) and will be fully retracted when inserted into the ear canal (i.e., normal body temperature). In another embodiment, where the action of the spring is based on the properties of bimetallics or phase change materials, the spring extends and retracts less gradually.

In FIGS. 4A and 4B the length of the spring 44' is shown as L' corresponding to its increased length due to a drop in its temperature.

The plunger 46 is preferably coated with a cerumen repellant material. This coating can be in the form of a hydrogel or other oleophobic material, which does not accumulate ear wax or other oils. Such a construction prevents cerumen from sticking to the plunger 46 after it has cleared away the cerumen 14 and other debris.

Figure 5A:
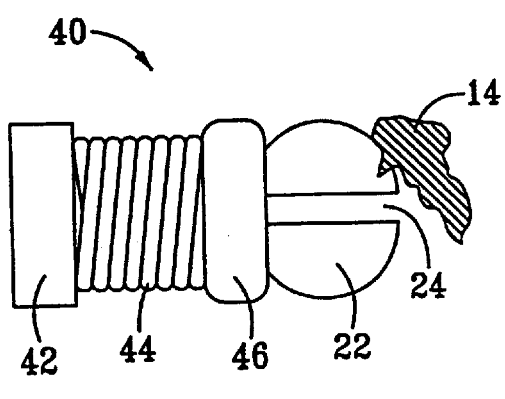
FIGS. 5A and 5B are top and side views, respectfully, of the cerumen guard of FIGS. 3A and 3B, upon returning to a retracted position.
Figure 5B:
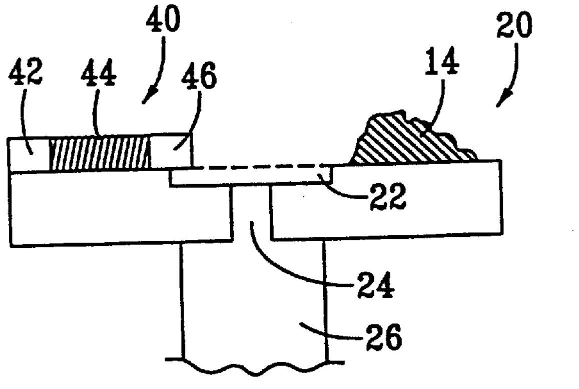

FIGS. 5A and 5B show the self-cleaning cerumen guard 40 after returning to a retracted state, previously shown in FIGS. 3A and 3B. In FIGS. 5A and 5B, however, the cerumen 14 has been cleared from the acoustic path.

Figure 6A:
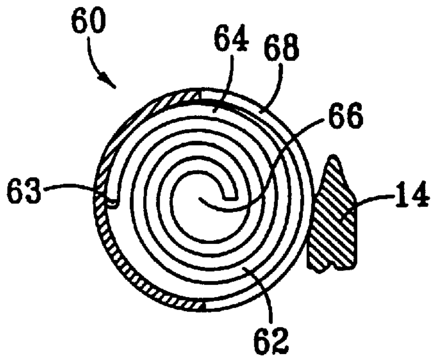
FIGS. 6A and 6B are top and side views, respectfully, of a second preferred embodiment of a self-cleaning cerumen guard constructed in accordance with the present invention, shown in a retracted position.
Figure 6B:
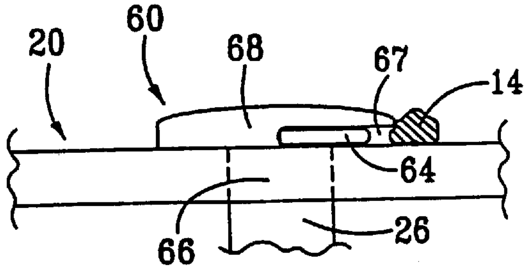

Turning to FIGS. 6A and 6B, a second preferred self-cleaning cerumnen guard 60 constructed in accordance with the present invention is shown. The principles of operation of the cerumen guard 60 are similar to that of the cerumen guard 40, described in conjunction with FIGS. 3–5. Most notably, a thermally activated material is employed to automatically clear a sound port 66 of cerumen and debris upon a change in temperature. In particular, the thermally activated material is calibrated so that automatic cleaning will occur when the hearing device 18 is removed from an ear canal 10.

The cerumen guard 60 comprises a coiled spring 64 formed from a thermally activated material. A first end 63 of the coiled spring 64 is connected to the inside surface of a slotted cover 68. The slotted cover 68 covers both the spring 64 and the sound port 66. The cover 68 provides additional protection to the sound port 66, while also providing an opening (slot) 67 so that acoustic energy can reach the sound port 66.

FIGS. 6A and 6B show the self-cleaning cerumen guard 60 in a retracted state. While seated within a user's ear canal 10, the self-cleaning cerumen guard 60 remains in this retracted position and does not obstruct the acoustic path to the sound port 66. In FIGS. 6A and 6B, the sound port 66 is blocked by a piece of cerutnen 14, typical of the situation where a hearing device has been positioned in an ear canal for an extended period of time.

Figure 7A:
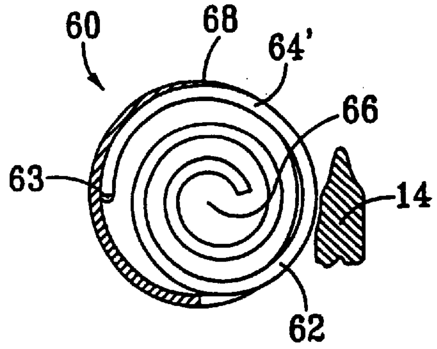
FIGS. 7A and 7B are top and side views, respectfully, of the cerumen guard of FIGS. 6A and 6B, shown in an extended position.
Figure 7B:
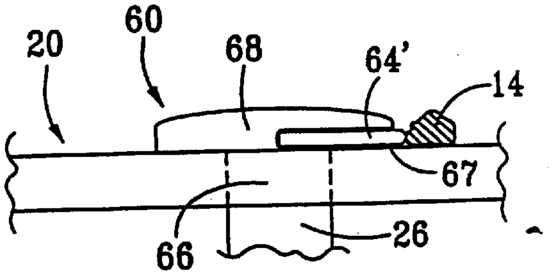

Turning to FIGS. 7A and 7B, the cerumen guard 60 is shown in an extended state. When activated by a decrease in temperature, the coiled spring 64 extends into what is shown in FIGS. 7A and 7B as reference number 64'. This extension forces an outer ring 62 of the coiled spring 64' across the sound port 66, thereby wiping any accumulated cerumen 14 or other debris from the acoustic path. The coiled spring 64' is oriented so that it will extend upon a decrease in temperature. As such, when the hearing device 18 is removed from the ear canal 10, the coiled spring 64 extends and the outer ring 62 is forced across the distal end 20 of the hearing device 18.

Conversely, when the hearing device 18 is inserted into the ear canal 10, the resulting increase in temperature causes the coiled spring 64 to retract, thereby moving the outer ring 62 away from the sound port 66. The acoustic path is therefore unobstructed when the hearing device 18 is in operation within a user's ear canal. As will be appreciated by those of ordinary skill in the art, the particular temperatures at which the spring 64 extends or retracts may be varied by utilizing different thermally activated materials.

Where the action of the spring 64 is based on simple thermal expansion and contraction, the spring 64 will gradually extend and retract when moved between two temperature ranges and is preferably formatted so that it will be fully extended when removed from the ear canal (i.e. room temperature) and will be fully retracted when inserted into the ear canal (i.e. normal body temperature). In another embodiment, where the action of the spring is based on the properties of certain bimetallics or phase change materials, the spring extends and retracts less gradually.

The outer ring 62 is preferably coated with a cerumen repellant material. This coating can be in the form of a hydrogel or other oleophobic material, which does not accumulate ear wax or other oils. Such a construction prevents cerumen from sticking to the outer ring 62 after it has cleared away the cerumen 14 and other debris.

Figure 8A:
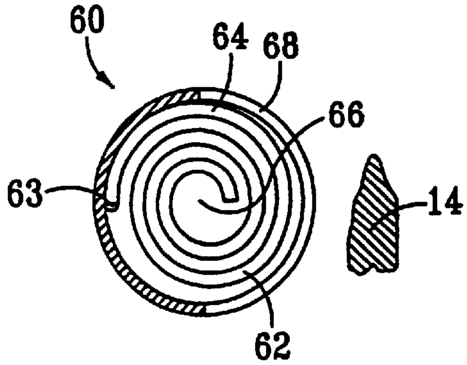
FIGS. 8A and 8B are top and side views, respectfully, of the cerumen guard of FIGS. 6A and 6B, upon returning to a retracted position.
Figure 8B:
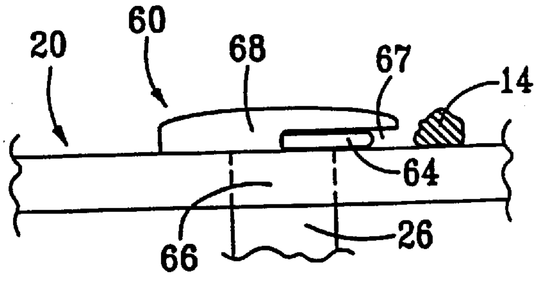

FIGS. 8A and 8B show the cerumen guard 60 after it returns to a retracted state previously shown in FIGS. 6A and 6B. In FIGS. 8A and 8B, however, the cerumen 14 has been cleared from the acoustic path.

Figure 9A:
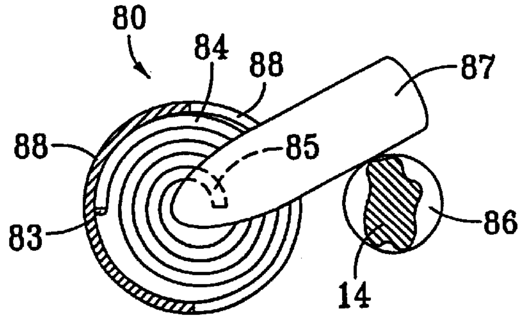
FIGS. 9A and 9B are top and side views of a third preferred embodiment of a self-cleaning cerumen guard constructed in accordance with the present invention, shown in a retracted position.
Figure 9B:
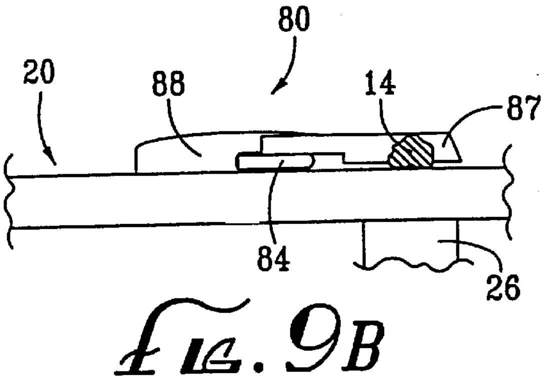

Turning to FIGS. 9A and 9B, a third preferred embodiment of a self-cleaning cerumen guard 80 constructed in accordance with the present invention is shown. The principles of operation of the self-cleaning cerumen guard 80 are similar to that of the self-cleaning cerumen guard 60 described in conjunction with FIGS. 6–8, as well as the self-cleaning cerumen guard 40 described in conjunction with FIGS. 3–5. Again, a thermally activated material is employed in its construction to automatically clear a sound port 86 of cerumen and debris upon a change in temperature, wherein the thermally activated material is preferably calibrated so that automatic cleaning will occur when the hearing device 18 is removed from an ear canal 10.

The cerumen guard 80 comprises a coiled spring 84 formed from a thermally activated material. A first end 83 of the coiled spring 84 is connected to the inside surface of a slotted cover 88. The slotted cover 88 covers the spring 84 and a plunger 87 is mounted to a centrally disposed second end 85 of the coiled spring portion 84. As seen in FIGS. 9A and 9B, the cerumen guard 80 remains in a retracted state while seated within a user's ear canal 10. Therefore, the plunger 87 does not obstruct the acoustic path to the sound port 86. In FIGS. 9A and 9B the sound port 86 is shown blocked by a piece of cerumen 14, typical of the situation where a hearing device has been positioned in an ear canal for an extended period of time.

Figure 10A:
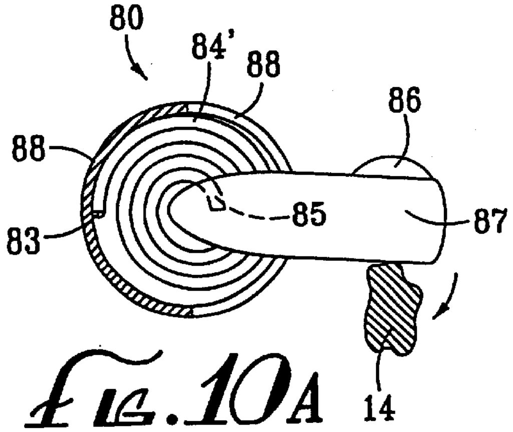
FIGS. 10A and 10B are top and side views, respectfully, of the cerumen guard of FIGS. 9A and 9B, shown in an extended position.
Figure 10B:
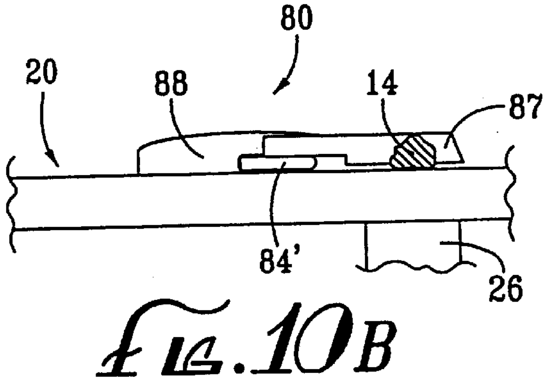

Turning to FIGS. 10A and 10B, the cerumen guard 80 is shown in anextended state. When activated by a decrease in temperature, the coiled spring portion 84 extends into what is shown in FIGS. 10A and 10B as reference number 84'. This extension forces the plunger 87 across the sound port 86, thereby wiping any accumulated cerumen 14 or other debris from the acoustic path. The coiled spring 84 is oriented so that it will extend upon a decrease in temperature. As such, when the hearing device 18 is removed from the ear canal 10, the spring 84 extends and the plunger 87 is forced across the distal end 20 of the hearing device 18.

Conversely, when the hearing device 18 is inserted into the ear canal 10, the resulting increase in temperature causes the coiled spring 84 to retract, thereby moving the plunger 87 away from the sound port 86. The acoustic path is therefore unobstructed when the hearing device 18 is in operation within a user's ear canal. As will be appreciated by those of ordinary skill in the art, the particular temperature at which the spring extends or retracts may be varied by utilizing different thermally activated materials.

Where the action of the spring 84 is based on simple thermal expansion and contraction, the spring 84 will gradually extend and retract when moved between two temperature ranges and is preferably formatted so that it will be fully extended when removed from the ear canal (i.e. room temperature) and will be fully retracted when inserted into the ear canal (i.e. normal body temperature). In another embodiment, where the action of the spring is based on the properties of certain bimetallics or phase change materials, the spring extends and retracts less gradually.

The plunger 87 is preferably coated with a cerumen repellant material. This coating can be in the form of a hydrogel or other oleophobic material, which does not accumulate ear wax or other oils. Such a construction prevents cerumen from sticking to the plunger 87 after it has cleared away the cerumen 14 and other debris.

Figure 11A:
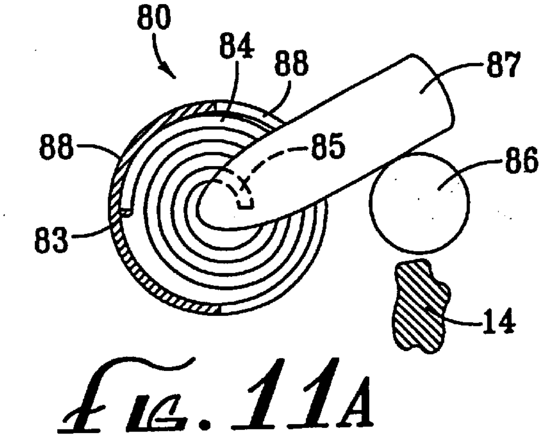
FIGS. 11A and 11B are top and side views of the cerumen guard of FIGS. 9A and 9B, upon returning to a retracted position.
Figure 11B:
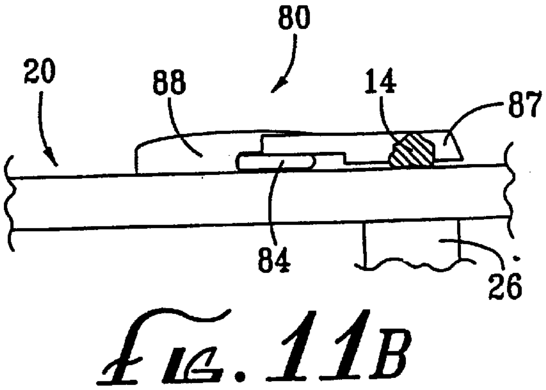

FIGS. 11A and 11B show the cerumen guard 80 after returning to a retracted state previously shown in FIGS. 9A and 9B. In FIGS. 11A and 11B, however, the cerumnen 14 has been cleared from the acoustic path.

Figure 12:
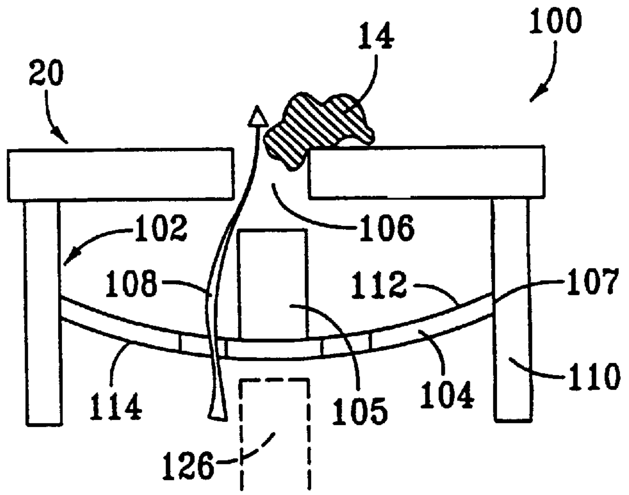
FIG. 12 is a side view of a fourth preferred embodiment of a self-cleaning cerumen guard constructed in accordance with the present invention, shown in a first position.
Figure 13:
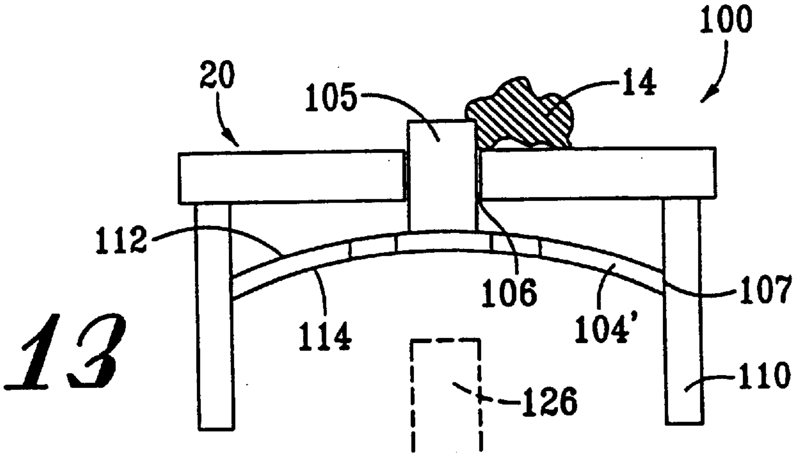
FIG. 13 is a side view of the self-cleaning cerumen guard of FIG. 12, shown in a second position.
Figure 14:
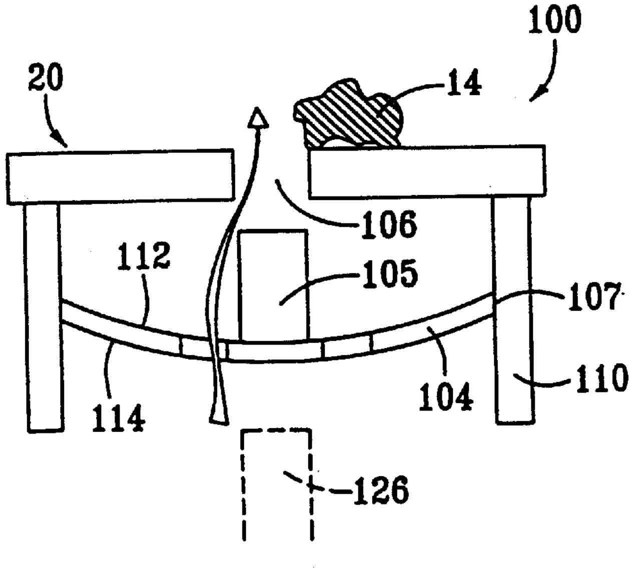
FIGS. 14 is a side view of the self-cleaning cerumen guard of FIG. 12, upon returning to the first position.

FIGS. 12–14 show a fourth preferred self-cleaning cerumen guard 100 constructed in accordance with the present invention. In this embodiment, a disk 104 formed from a thermally activated material is positioned within a receiver housing 110 and below the distal end 20 of a hearing device 18. The disk 104 includes an upper surface 112, a lower surface 114, and a circumferential surface 107. The circumferential surface 107 of the disk 104 is connected to an interior surface 102 of the receiver housing 110. Fixed to the center of the upper surface 112 facing the distal end 20 of the hearing device 100, is a cylindrically shaped plunger 105. The it plunger 105 is aligned with a corresponding sound port 106. Acoustic energy travels from a receiver 126, through the sound port 106 to the tympanic membrane. Arrow 108 represents a typical sound path. Preferably, the disk does not block sound waves from travelling between the receiver 126 and the tympanic membrane. For instance, the disk can be formed from an acoustically transparent material. Alternately, the disk can be slotted or perforated to allow sound waves to efficiently reach the tympanic membrane.

Preferably, the disk 104 is formed from a bimetallic or phase change material. The geometry of the disk 104 therefore rapidly changes when the disk temperature moves from one temperature range to another. The thermally activated material is formatted so that when inserted into an ear canal, the upper surface 112 of the disk 104 maintains a concave profile. FIG. 12 shows the positioning of the self-cleaning cerumen guard 100 when inserted in an ear canal. In this position, the plunger 105 does not interfere with the sound port 106 and the acoustic path 108 is unobstructed. FIG. 12 also shows a piece of cerumen 14 partially blocking the sound port 106.

FIG. 13 represents the action of the disk 104 when its temperature changes. Upon changing from one temperature range to another, the disk 104 changes shape, reversing the direction of the concave surface. The resulting shape of the disk is represented as reference number 104'. Since the circumferential surface 107 of the disk 104' is connected to the interior wall 102 of the receiver housing 110, the temperature change of the disk 104 causes the lower surface 114 to assume a concave profile, thereby forcing the plunger 105 through the sound port 106 and clearing away the cerumen 14 which had been previously obstructing the sound path 108. This action is representative of what occurs when the hearing device is removed from the ear canal and is exposed to an ambient temperature. As an example, the thermally activated material of the disk 104 can maintain a first shape when its temperature is in the range of 95° F. or higher and a second shape when its temperature is in the range of 90° F. or lower. As will be appreciated by those skilled in the art, various temperature ranges can be used to accommodate changing ambient temperatures or other variables that may exist. Further, the temperature ranges may abut each other so that the transition from the first shape to the second shape occurs less gradually.

FIG. 14 shows the same hearing device 18 after being inserted back into an ear canal 10. With the resulting increase in temperature, the disk 104 returns to its previous shape and the upper surface 112 again assumes a concave profile. In FIG. 14, after the cerumen 14 has been cleared from the sound port 106, there are no obstructions to interfere with the operation of the hearing device 18.

The self-cleaning cerumen guard of the present invention is not limited to use with any specific type of hearing device. In particular, while the invention has been described in conjunction with an in-the-canal type of hearing device such as a completely in-the-canal device, it is equally well suited to be used with various other types of hearing device which are seated within portions of the ear canal that are susceptible to the build up of cerumen and other debris.

Figure 15A:
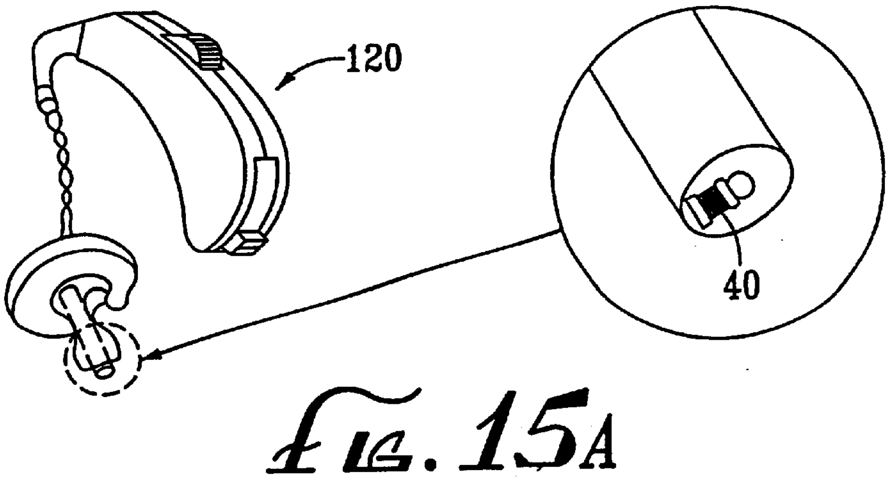
FIGS. 15A–15D show a preferred embodiment of the self-cleaning cerumen guard of the present invention, while mounted to various types of hearing devices.
Figure 15B:
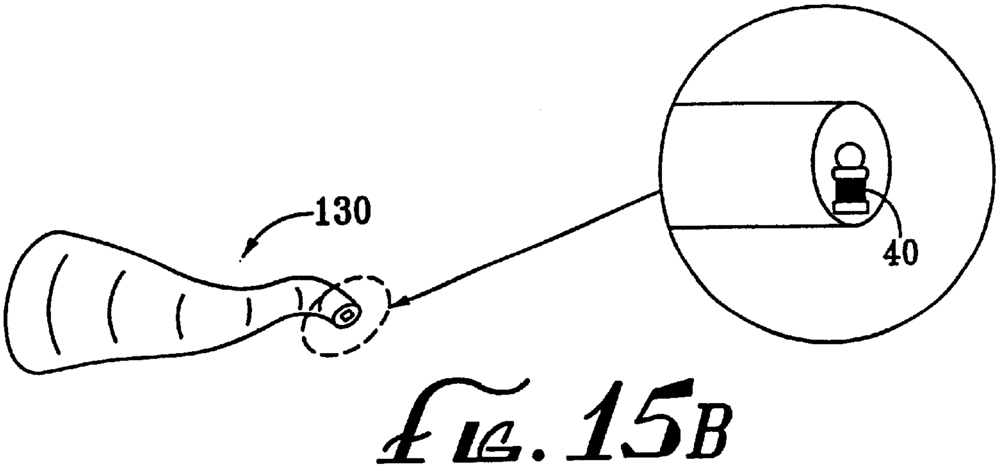
Figure 15C:
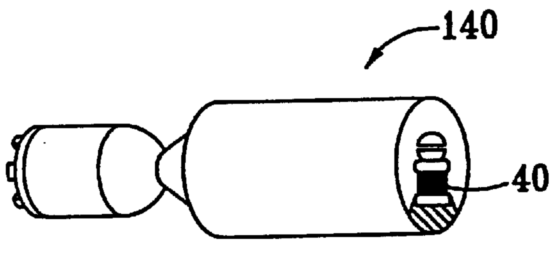
Figure 15D:
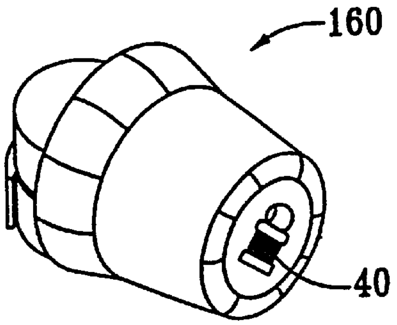

FIGS. 15A–15D show the self-cleaning hearing device of the present invention as used in conjunction with a variety of different types and styles of hearing devices. The self-cleaning hearing device 40 of the present invention can be used with a Behind-the-ear (BTE) type hearing device 120 (FIG. 15A), a molded, hard shell hearing device 130 (FIG. 15B), a partially In-the-Canal (ITC) type hearing device 140 (FIG. 15C), as well as a Completely-in-the-Canal (CIC) type hearing device 160 (FIG. 15D). Further, any of the various embodiments of the self-cleaning cerumen guards described above can be incorporated onto the distal ends of any type of hearing device.

Although the present invention has been described and illustrated in the above description and drawings, it is understood that this description is by example only and that numerous changes and modifications can be made by those skilled in the art without departing from the true spirit and scope of the invention. The invention, therefore, is not to be restricted, except by the following claims and their equivalents.

What is claimed is:

1. A hearing device, comprising:

a cerumen remover mounted on the hearing device, the cerumen remover comprising a thermally activated material;

wherein the cerumen remover clears away accumulated cerumen from the hearing device in response to a temperature change.

2. The hearing device of claim 1, wherein the cerumen remover is mounted on a distal end of the hearing device.

3. The hearing device of claim 1, wherein the cerumen remover maintains a first shape in a first temperature range and a second shape in a second temperature range.

4. The hearing device of claim 1, wherein the cerumen remover is generally elongate and is in a retracted position in a first temperature range and is in an extended position in a second temperature range.

5. The hearing device of claim 1, wherein the cerumen remover has a first end and a second end, wherein the cerumen remover is circularly wound having an outer ring, and oriented such that the first end is radially disposed and the second end is centrally disposed.

6. The hearing device of claim 1, the hearing device including a housing having an interior surface, the cerumen remover further comprising a disk having a circumferential surface, an upper surface, and a lower surface, wherein the circumferential surface of the disk is connected to the interior surface of the housing.

7. The hearing device of claim 6, further comprising a generally elongate plunger having a first end and a second end, wherein the first end is connected to the upper surface of the disk.

8. The hearing device of claim 3, wherein the first temperature range is approximately 95° F. and higher, and the second temperature range is approximately 90° F. and lower.

9. The hearing device of claim 3, wherein the first temperature range is approximately 90° F. and lower, and the second temperature range is approximately 95° F. and higher.

* * * * *